United States Patent [19]

Tachibana et al.

[11] Patent Number: 5,440,914
[45] Date of Patent: Aug. 15, 1995

[54] METHOD OF MEASURING DISTRIBUTION AND INTENSITY OF ULTRASONIC WAVES

[76] Inventors: Katsuro Tachibana; Shunro Tachibana, both of 6-18, Kusagae 1-chome, Chuo-ku, Fukuoka-shi, Fukuoka-ken, Japan

[21] Appl. No.: 277,822

[22] Filed: Jul. 20, 1994

[30] Foreign Application Priority Data

Jul. 21, 1993 [JP] Japan ................................. 5-180386

[51] Int. Cl.$^6$ ........................................... G01N 29/00
[52] U.S. Cl. ..................................... 73/1 DV; 367/13
[58] Field of Search ............ 73/1 DV, 649, 645, 646; 367/13; 181/139; 381/58

[56] References Cited

U.S. PATENT DOCUMENTS 2,803,128  8/1957  Petermann ............................. 367/13
4,681,119  7/1987  Rasor et al. ........................... 128/660

*Primary Examiner*—Robert Raevis
*Attorney, Agent, or Firm*—Keck, Mahin & Cate

[57] ABSTRACT

There is provided a method of measuring three-dimensional distribution of ultrasonic waves which allows simple real time measurement, wherein a multiplicity of bubble-shaped elements, which are trace amounts of gas coated with an extremely thin coating, are dispersed in a liquid; an ultrasonic oscillation element is placed in the liquid to radiate ultrasonic waves; the bubble-shaped elements are collapsed by the radiation of the ultrasonic waves; and changes in the optical characteristics of the liquid caused by the collapse of the bubble-shaped elements are visually measured.

1 Claim, 3 Drawing Sheets

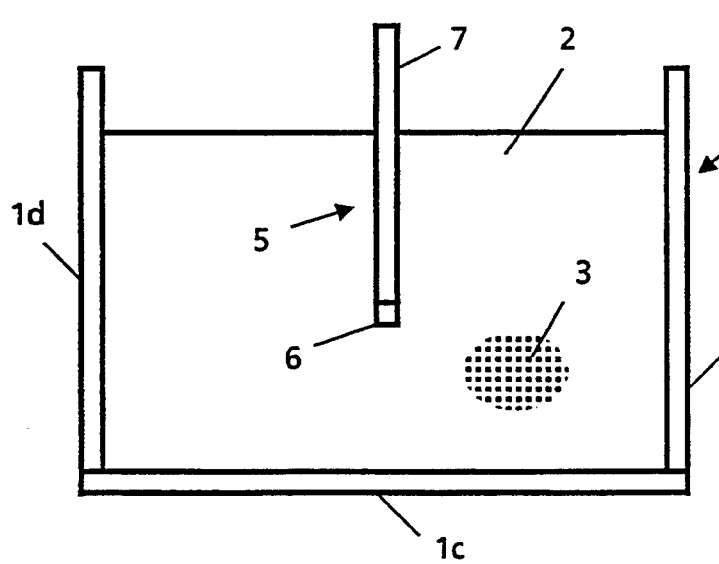
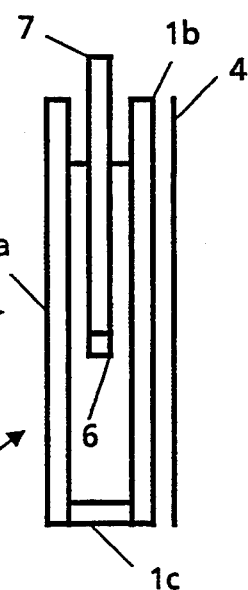
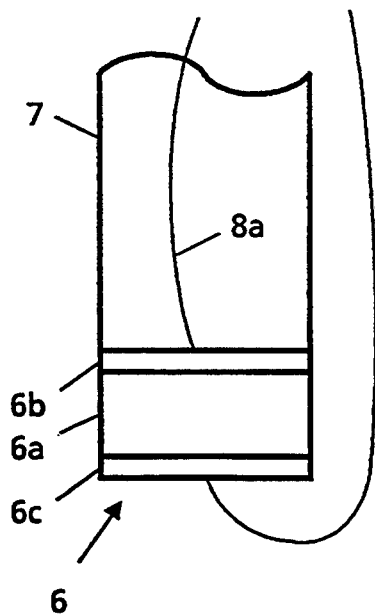
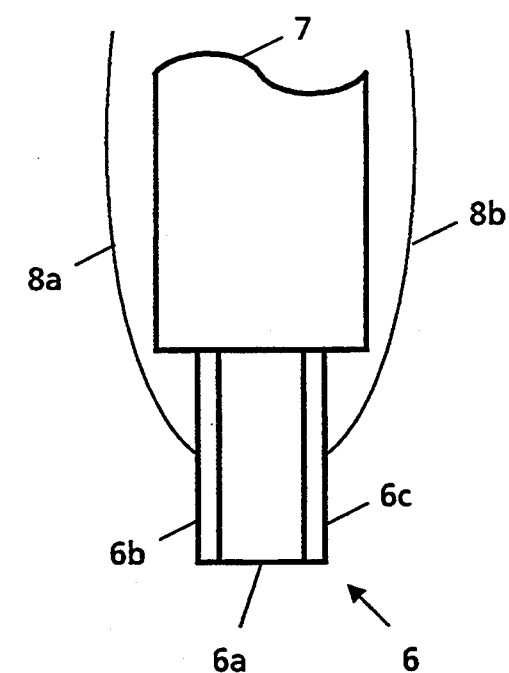

METHOD OF MEASURING DISTRIBUTION AND INTENSITY OF ULTRASONIC WAVES

BACKGROUND OF THE INVENTION

1. Field of the Invention

The present invention relates to a method of measuring the distribution and intensity of ultrasonic waves used for ultrasonic diagnosis apparatuses and ultrasonic remedial apparatuses.

2. Prior Art

It is important to know the distribution and intensity of ultrasonic waves radiated by an ultrasonic diagnosis apparatus in studying the effect of the ultrasonic waves on an organism and in evaluating the ultrasonic diagnosis apparatus.

For an ultrasonic remedial apparatus, it is necessary to check the radiation characteristics of the remedial ultrasonic oscillation element because the radiation of ultrasonic waves must be concentrated in the direction of the diseased part. Further, even if the desired characteristics can be obtained at a particular frequency, those characteristics may change at another frequency. Therefore, one must have an understanding of the characteristics at varied frequencies.

Various methods of measuring the intensity and distribution of ultrasonic waves are conventionally known.

For example, an ultrasonic microphone is placed in a liquid in which ultrasonic waves are radiated and measured for intensity at the position where the microphone is placed. The distribution of the intensity can be also measured by changing the position of the ultrasonic microphone.

However, the measuring method utilizing an ultrasonic microphone has problems as described below. (1) Since an ultrasonic microphone having a certain volume is placed in the liquid, the presence of the ultrasonic microphone itself disturbs the distribution of the ultrasonic waves, thereby preventing accurate measurement of the distribution of the intensity. (2) Since an ultrasonic microphone generally has a narrow frequency band, it does not allow measurement of the intensity and distribution of ultrasonic waves in a wide frequency band. (3) In general, an ultrasonic microphone has directivity specific thereto. Therefore, the result of measurement varies depending on the orientation of the ultrasonic microphone. (4) The characteristics of the ultrasonic oscillation element can not be intuitively understood from the numerical data measured. This necessitates processes such as the graphing of the data. (5) Even if a graph is used, it is difficult to obtain three-dimensional representation of the intensity and distribution of ultrasonic waves. (6) Real time observation of three-dimensional changes in the intensity and distribution of ultrasonic waves is not possible.

In addition to the above described measuring method utilizing an ultrasonic microphone, there are well-known optical approaches such as the Schlieren method wherein changes in the refractive index due to radiation of ultrasonic waves are optically detected. Such optical approaches allow visualized measurement of the distribution of the sound field without disturbance to the state of the object to be measured caused by the measuring apparatus itself.

However, such optical approaches require a special light source and an imaging optical system such as a lens which make the measuring apparatus undesirably large.

There is another known method which utilizes the fact that application of ultrasonic waves to a certain substance causes the substance to emit a very small amount of light, i.e., the acoustic luminescence phenomenon, to measure three-dimensional distribution of the ultrasonic waves by way of photographs with long exposures. However, this method does not allow direct visualization and requires the photographic and development processes, which means that the measurement takes longer than is desirable.

Under such circumstances, it is an object of the present invention to provide a method of measuring three-dimensional distribution of ultrasonic waves which allows simple real time measurement.

SUMMARY OF THE INVENTION

According to the present invention, the above-described object is achieved by dispersing a multiplicity of bubble-shaped elements which are trace amounts of gas with an extremely thin coating in a liquid, radiating ultrasonic waves in the liquid by placing an ultrasonic oscillation element in said liquid, collapsing the bubble-shaped elements by way of the radiation of the ultrasonic waves, and visually measuring changes in optical characteristics of the liquid caused by the collapse of the bubble-shaped elements.

When a multiplicity of bubble-shaped elements each coated with an extremely thin film of protein or the like are dispersed in a liquid in a transparent container, optical reflections at the surface of the bubble-shaped elements render the liquid cloudy. If ultrasonic waves are applied to the liquid containing the bubble-shaped elements, the ultrasonic energy causes cavitation of the bubble-shaped elements. As a result, the bubble-shaped elements are collapse and the gas inside dissolves in the liquid. This eliminates the reflection of light at the surface of the bubble-shaped elements and consequently renders the liquid transparent in the areas where the elements have collapsed. Therefore, the areas where the liquid becomes transparent represent the pattern of the application of the ultrasonic waves, the transparency of such areas indicating the intensity of the ultrasonic waves.

BRIEF DESCRIPTION OF THE DRAWINGS

FIGS. 1 (a) and 1 (b) schematically illustrate an apparatus for measuring the intensity and distribution of ultrasonic waves for carrying out the present invention.

FIGS. 2(a) and 2(b) are typical views showing how to mount an ultrasonic oscillation element to a support element of a part to be measured.

DETAILED DESCRIPTION OF THE PREFERRED EMBODIMENT

Figure 3:
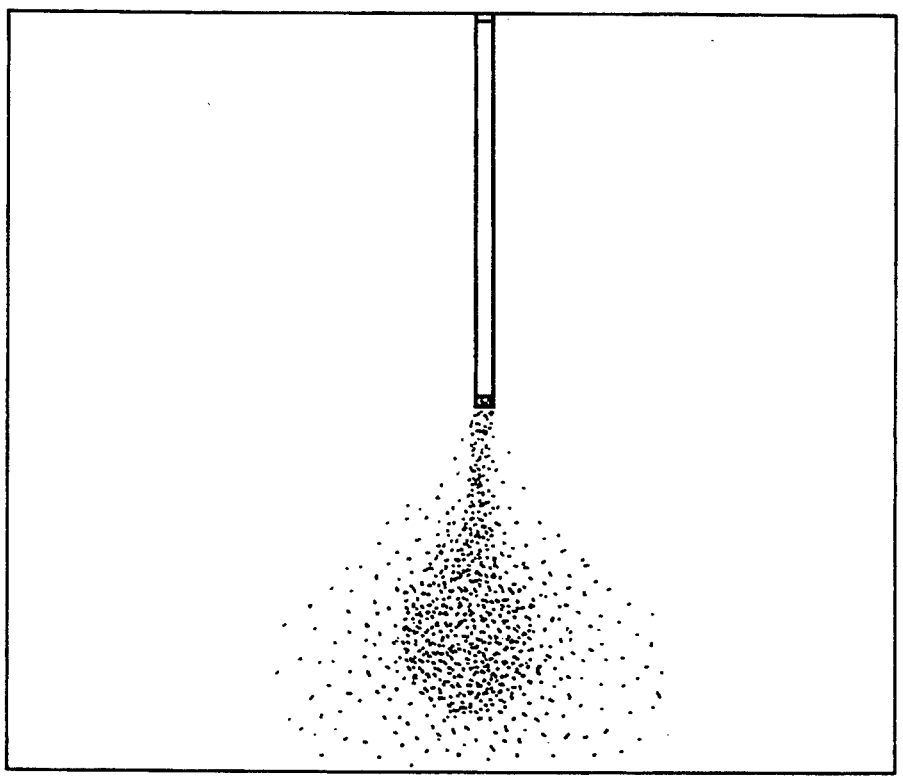
FIG. 3 illustrates an example of a pattern of the application of ultrasonic waves using an ultrasonic oscillation element having a horizontal oscillation surface.

The features of the present invention will now be specifically described based on an embodiment thereof with reference to the accompanying drawings.

FIG. 1 schematically illustrates an apparatus for measuring the intensity and distribution of ultrasonic waves for carrying out the present invention. FIG. 1(a) is a front view, and FIG. 1(b) is a sectional view.

A transparent container 1 is constructed by disposing a pair of transparent plates 1a and 1b made of glass, synthetic resin or the like so that they face each other in parallel, and by mounting spacers 1c, 1d and 1e between the transparent plates 1a and 1b using an adhesive or the like to regulate the distance between the transparent plates 1a and 1b and to make the three sides watertight. For example, the spacing between the transparent plates 1a and 1b may be about 7-15 mm. This transparent container 1 may be integrally formed of glass, synthetic resin or the like.

In the transparent container 1, a liquid 2 such as a physiological saline is filled and a multiplicity of bubble-shaped elements 3 which are trace amounts of gas coated with a very thin film of protein or the like, are substantially uniformly dispersed. For bubble-shaped elements 3, Albunex (product name) from MBI Corp., USA may be used. The bubble-shaped elements 3 are diffused in the liquid 2 in concentrations such that 0.5-4 hundreds of millions of the same exist in 1 cc. The spacing between the transparent plates 1a and 1b of the transparent container 1 and the concentration of the bubble-shaped elements are set to values such that it can be clearly seen that the liquid becomes transparent when the bubble-shaped elements 3 collapse as a result of the application of ultrasonic waves as described later. Although FIG. 1 shows the bubble-shaped elements 3 for convenience in explanation as a multiplicity of separate points, the bubble-shaped elements 3 actually have a very small diameter and exist in a very large number. Therefore, they appear as a cloudy liquid to human eyes, as will be described later.

A background plate 4 colored with, for example, a dark blue, black or the like in a uniform concentration is disposed along the outer surface of the transparent plate 1b of the transparent container 1. A common lighting device (not shown) such as an incandescent lamp or fluorescent lamp may be disposed as needed in front of the other transparent plate 1a of the transparent container 1.

A member to be measured 5 on which measurement of radiation characteristics are to be made is placed in the liquid 2 in the transparent container 1. The member to be measured 5 is constituted by an ultrasonic oscillation element 6 and a stick-shaped support element 7 for supporting the ultrasonic oscillation element 6.

FIG. 2 shows how to mount the ultrasonic oscillation element 6 to the support element 7 of the member to be measured. The ultrasonic oscillation element 6 is comprised of a piezoelectric member 6a made of a ceramic, a polymer film of the like in the form of a flat plate and electrodes 6b and 6c provided on both sides of the piezoelectric member 6a. Lead wires 8a and 8b are lead out from the electrodes 8a and 8b, respectively. Ultrasonic wave signals from an external ultrasonic wave signal generator (not shown) are supplied through the lead wires 8a and 8b to the electrodes 6b and 6c. This causes the piezoelectric member 6a to oscillate and, as a result, ultrasonic waves radiate from the ultrasonic oscillation element 6. The ultrasonic oscillation element 6 generally oscillates in the direction of the thickness of the piezoelectric member 6a, i.e., a direction perpendicular to the surface of the piezoelectric element 6a. FIG. 2(a) shows an example wherein the ultrasonic oscillation element 6 is mounted to the support element 7 so that an oscillation surface of the piezoelectric element 6a horizontally extends, while FIG. 2(b) shows an example wherein the ultrasonic oscillation element 6 is mounted to the support element 7 so that an oscillation surface of the piezoelectric element 6a vertically extends. In FIG. 2, the dimensions of each part of the ultrasonic oscillation element 6 are exaggerated for simplicity of illustration and are not drawn to scale.

When the ultrasonic oscillation element 6 is not supplied with the ultrasonic wave signals, the liquid 2 in the transparent container 1 uniformly appears cloudy as viewed in the direction of the arrow A in FIG. 1. The reason is that external light will be reflected by the surface of the multiplicity of bubble-shaped elements 3 and will be incident upon the eyes of the observer. Although the dark background plate 4 is disposed on the rear side of the transparent plate 1, the multiplicity of bubble-shaped elements 3 block the light path between the eyes of the observer and the background plate 4. As a result, the background plate 4 will not be directly visible and, even if visible, will be recognized only as a very light color.

When the ultrasonic wave signals are supplied to the ultrasonic oscillation element 6, the ultrasonic oscillation element 6 will radiate ultrasonic waves in the liquid 2, and the ultrasonic energy will cause cavitation of the bubble-shaped elements 3 in the liquid 2, which will collapse the bubble-shaped elements 3, causing the gas in the bubble-shaped elements 3 to dissolve into the liquid. Thus, there are no reflections of light at the surface of the bubble-shaped elements 3, and the liquid becomes transparent in the areas where the bubble-shaped elements have collapsed. Therefore, the areas wherein the liquid 2 has become transparent represent the pattern of the radiation of the ultrasonic waves. Those areas wherein the intensity of the ultrasonic waves radiated is higher will have higher transparency. Since the shell portions of the bubble-shaped elements 3 are very small, they have no substantial influence on the reflection of light.

Since the dark background plate 4 is disposed on the rear side of the transparent plate 1, the color of the background plate 4, e.g., dark blue, will be visible in the areas wherein the liquid 2 has become transparent when viewed in the direction of the arrow A. In other words, the transparent pattern is converted into a pattern of dark blue, which is much easier to see.

As described above, the present embodiment allows the radiation pattern of ultrasonic waves to be directly viewed by the naked eye without any special device, thereby allowing the intensity of the ultrasonic waves to be simply visually checked.

FIG. 3 shows a transparent pattern as shown in FIG. 2(a) obtained using an ultrasonic oscillation element 6 which is horizontally disposed and fixed to the support element 7 at the upper surface thereof, and an ultrasonic wave signal having a frequency of 800 kHz and a voltage of 20 V. In this case, the radiation pattern spreads directly down.

Figure 4:
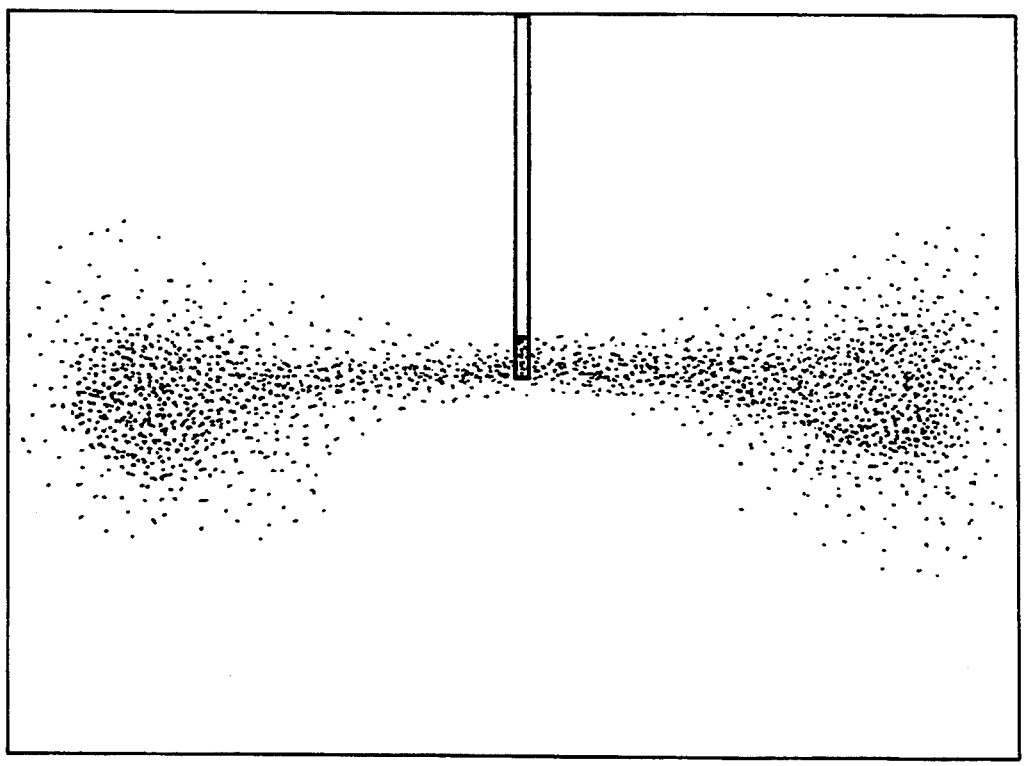
FIG. 4 illustrates an example of a pattern of the application of ultrasonic waves using an ultrasonic oscillation element having a vertical oscillation surface.

FIG. 4 shows a radiation pattern as shown in FIG. 2(b) obtained using an ultrasonic oscillation element 6 which is vertically disposed, serves as free oscillation surfaces at both sides thereof and is fixed to the support element 7 at a side edge thereof and an ultrasonic wave signal having a frequency of 800 kHz and a voltage of 20 V. In this case, the radiation pattern spreads horizontally.

Figure 5:
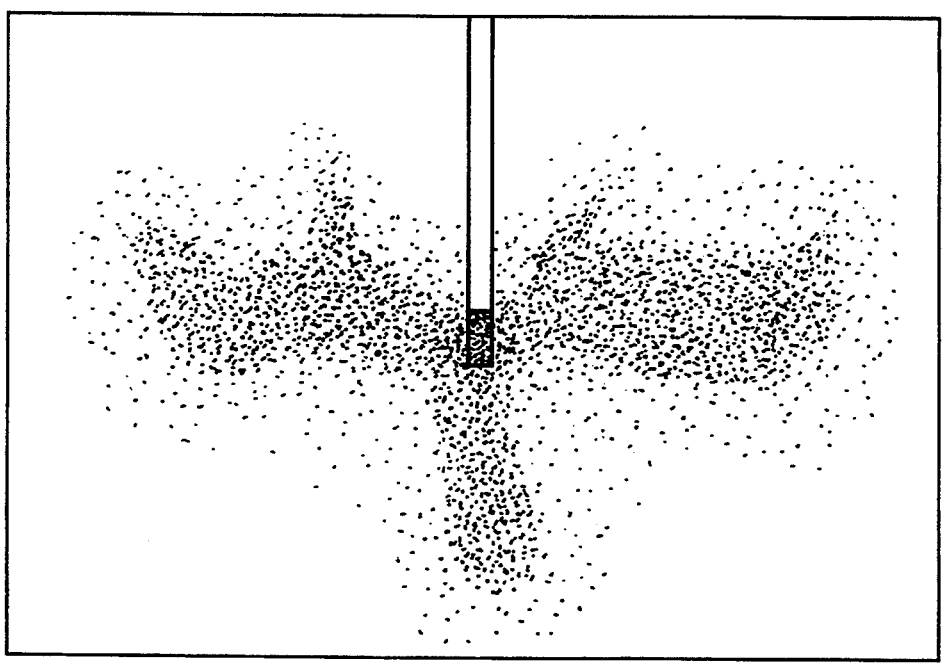
FIG. 5 illustrates another example of a pattern of the application of ultrasonic waves using an ultrasonic oscillation element having a vertical oscillation surface.

FIG. 5 shows a radiation pattern obtained in a case wherein the same ultrasonic oscillation element as that in FIG. 2(b) is used and wherein the frequency has been changed to 1300 kHz. In this case, the radiation pattern spreads in both the directly downward direction and the horizontal direction.

As is apparent from the above-mentioned figures, the transparent pattern greatly varies depending on the frequency, intensity and the like of the ultrasonic waves.

The present embodiment allows the three-dimensional state of the generation of ultrasonic waves to be very easily visually checked in real time. It is therefore possible to understand the characteristics of an ultrasonic oscillation element used for ultrasonic treatment or diagnosis in a very short time and, consequently, to easily design an ultrasonic oscillation element having the desired characteristics.

Although the transparent pattern is directly viewed by the naked eye in the above-described embodiment, the pattern may be indirectly measured using an ultrasonic diagnosis apparatus in a liquid which does not transmit light.

As described above, according to the present invention, the intensity of ultrasonic waves is visually measured according to the transparency of the liquid caused by the collapse of the bubble-shaped elements by the ultrasonic waves. Therefore, the characteristics of an ultrasonic oscillation element can be very simply measured in real time on a three-dimensional basis without using an elaborate apparatus.

The foregoing description of the preferred embodiment of the present invention has been presented for purposes of illustration and description. It is not intended to be exhaustive nor to limit the present invention to the precise form disclosed. Obviously many modifications and variations are possible without departing from the spirit and scope of the present invention as defined in the appended claim.

What is claimed is:

1. A method of measuring the intensity and distribution of ultrasonic waves comprising the steps of:
    dispersing a multiplicity of bubble-shaped elements, which are trace amounts of gas with an extremely thin coating, in a liquid;
    placing an ultrasonic oscillation element in said liquid to radiate ultrasonic waves, thereby collapsing said bubble-shaped elements; and
    visually measuring changes in the optical characteristics of said liquid caused by the collapse of said bubble-shaped elements.

* * * * *